(12) United States Patent
Kim et al.

(10) Patent No.: US 7,244,731 B2
(45) Date of Patent: Jul. 17, 2007

(54) 6-METHYLPYRIDINE DERIVATIVES, METHOD FOR PREPARING THEREOF AND ANTIVIRAL PHARMACEUTICAL COMPOSITION COMPRISING THE SAME

(75) Inventors: Jong-Woo Kim, Anyang-si (KR) Sang-Wook; Sang-Wook Lee, Anyang-si (KR); Geun-Hyung Lee, Yongin-si (KR); Jae-Jin Han, Yongin-si (KR); Sang-Jin Park, Yongin-si (KR); Eul-Yong Park, Yongin-si (KR); Joong-Chul Shin, Yongin-si (KR)

(73) Assignee: B & C Biopharm, Gyeonggi-do (KR)

( * ) Notice: Subject to any disclaimer, the term of this patent is extended or adjusted under 35 U.S.C. 154(b) by 199 days.

(21) Appl. No.: 10/528,461

(22) PCT Filed: Oct. 2, 2003

(86) PCT No.: PCT/KR03/02034

§ 371 (c)(1),
(2), (4) Date: Mar. 21, 2005

(87) PCT Pub. No.: WO2004/033450

PCT Pub. Date: Apr. 22, 2004

(65) Prior Publication Data

US 2006/0269609 A1    Nov. 30, 2006

(30) Foreign Application Priority Data

Oct. 11, 2002    (KR) ...................... 10-2002-0061994

(51) Int. Cl.
*A61K 31/5377* (2006.01)
*C07D 413/02* (2006.01)

(52) U.S. Cl. .................... 514/235.5; 544/131
(58) Field of Classification Search ................ 544/131; 514/235.5
See application file for complete search history.

(56) References Cited

U.S. PATENT DOCUMENTS 3,878,206 A    4/1975    Spencer et al.

7,087,758 B2 *    8/2006    Bryan et al. ................ 546/161

FOREIGN PATENT DOCUMENTS

EP    0 187 705    7/1986
WO    WO 01/78648 A2    10/2001

* cited by examiner

*Primary Examiner*—Joseph K. McKane
*Assistant Examiner*—Jason M. Nolan
(74) *Attorney, Agent, or Firm*—The Nath Law Group; Gary M. Nath; Susanne M. Hopkins

(57) ABSTRACT

The present invention relates to 6-methylpyridine derivatives useful as an antiviral agent. More particularly, the present invention relates to novel 6-methylpyridine derivatives having an excellent inhibitory effect on replication of Hepatitis C virus (HCV), or pharmaceutically acceptable salts thereof, to a method for preparing thereof, and to an antiviral pharmaceutical composition comprising the compound as an active ingredient. The 6-methylpyridine derivatives of the present invention have an excellent inhibitory effect on replication of hepatitis C virus and thus can be advantageously used as a therapeutic or prophylactic agent of hepatitis C

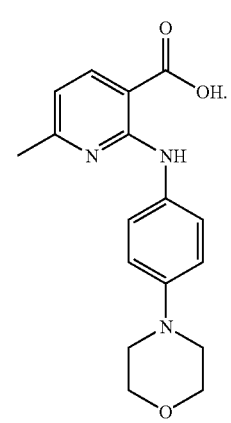

(I)

3 Claims, 3 Drawing Sheets

Figure 1:
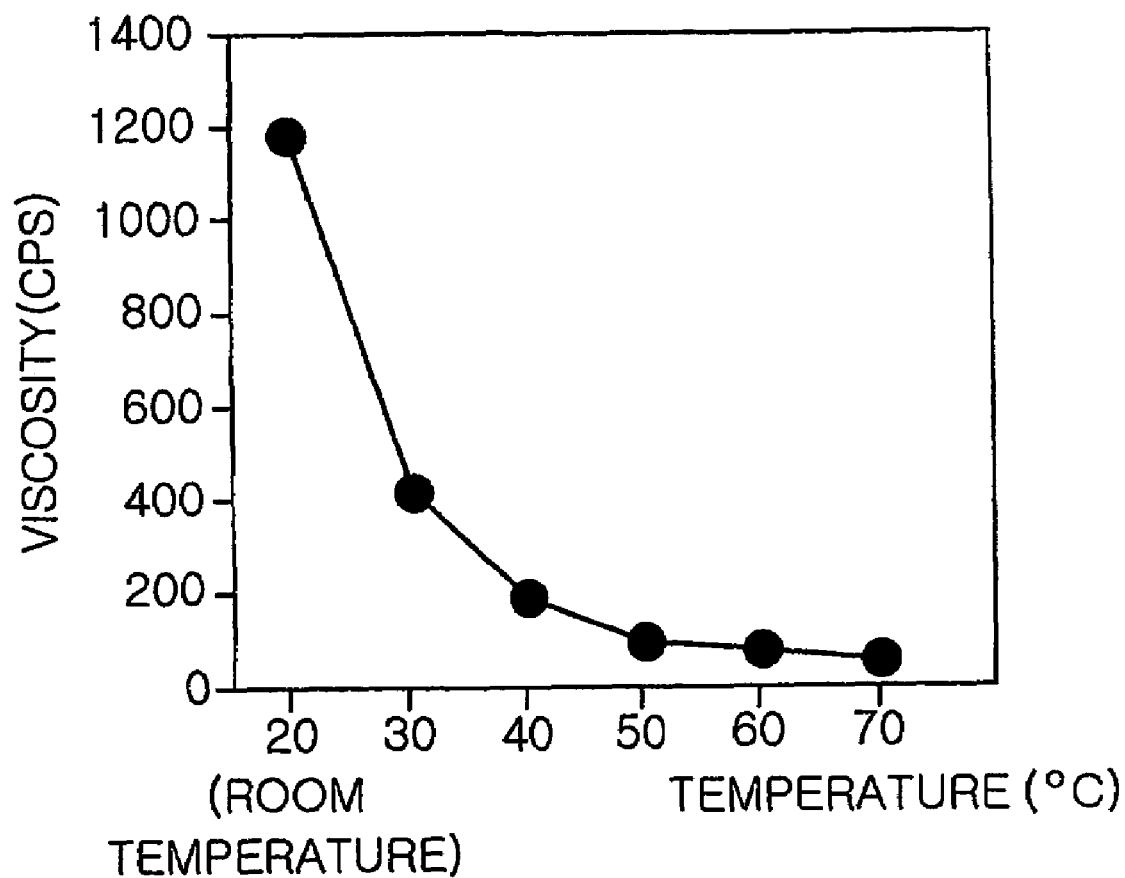
Figure 2A:
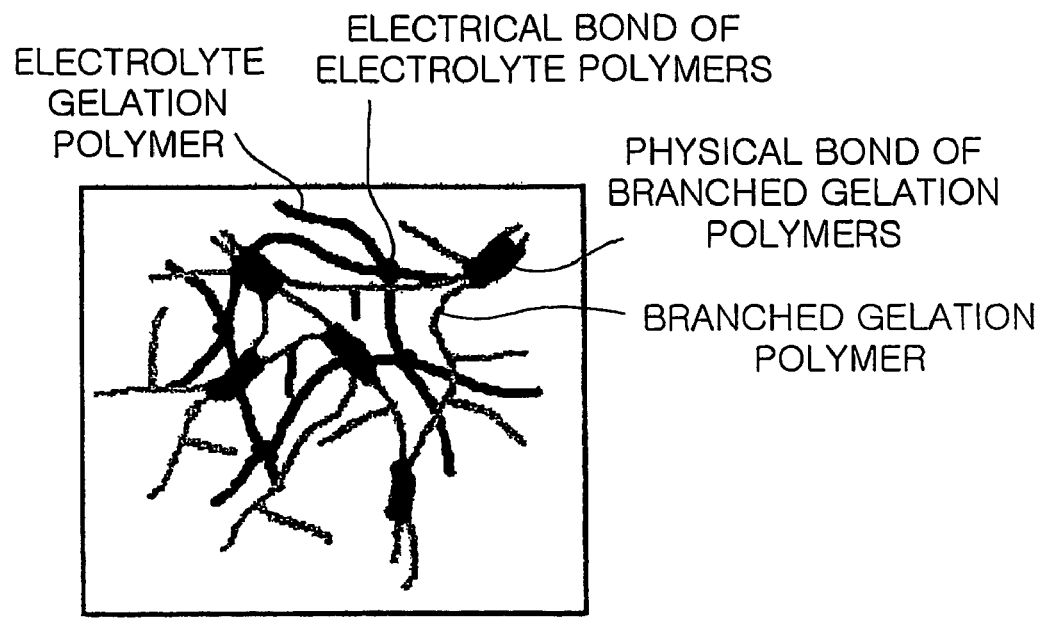
Figure 2B:
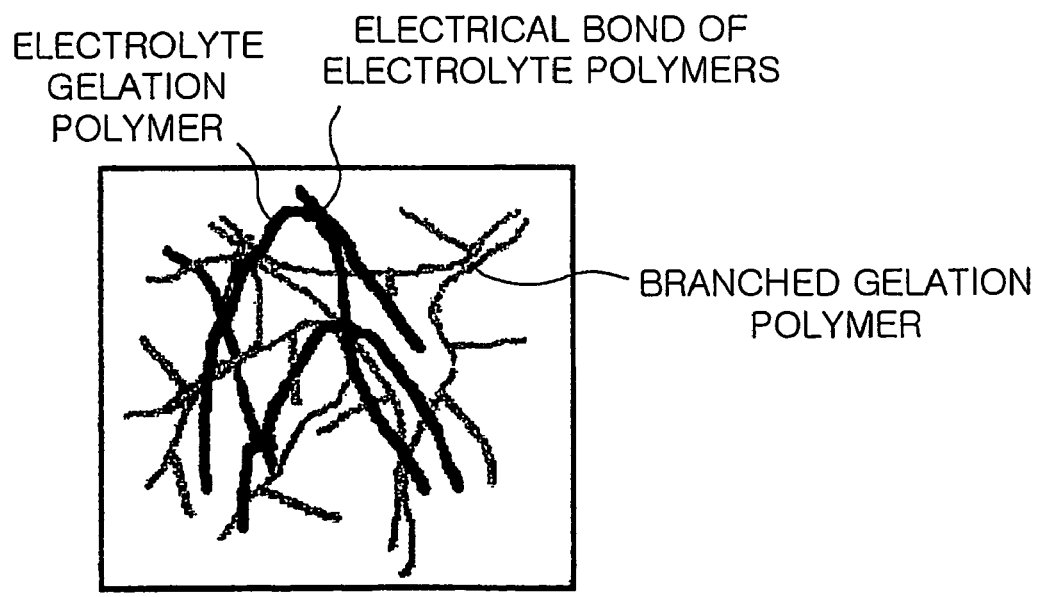
Figure 3:
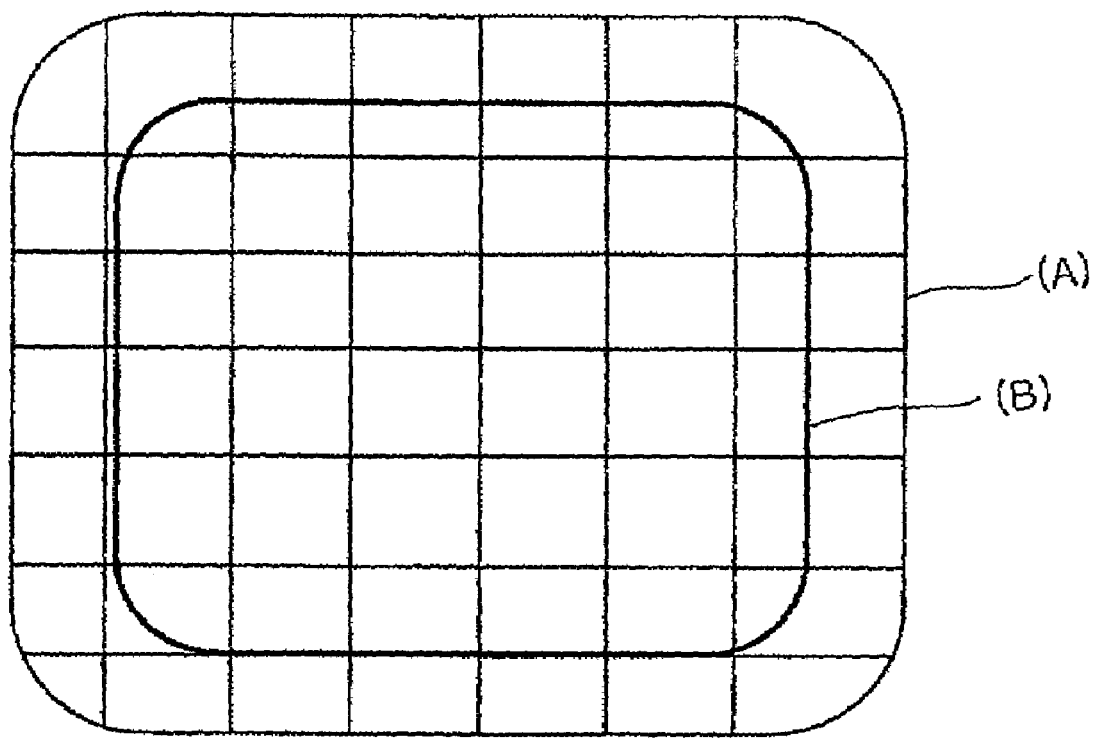

6-METHYLPYRIDINE DERIVATIVES, METHOD FOR PREPARING THEREOF AND ANTIVIRAL PHARMACEUTICAL COMPOSITION COMPRISING THE SAME

FIELD OF THE INVENTION

The present invention relates to 6-methylpyridine derivative useful as an antiviral agent, and more particularly novel 6-methylpyridine derivative having an excellent inhibitory effect on replication of Hepatitis C virus (HCV), represented by the following formula I:

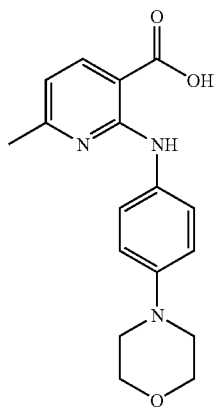

(I)

or pharmaceutically acceptable salts thereof, to a method for preparing thereof, and to an antiviral pharmaceutical composition comprising the compound as an active ingredient.

DESCRIPTION OF THE RELATED ART

Hepatitis C virus (HCV) is the major etiological agent of non-A and non-B viral hepatitis, mainly being post-transfusion and community-acquired. Once infected with HCV, approximately 80% of infected people, given its symptom is manifested, progress to chronic hepatitis, and the rest 20% of infected people progress to acute hepatitis causing hepatic cirrhosis, which is eventually transferred to liver cancer. According to a recently published report, more than 200 million worldwide are infected with HCV. For instance, more than 4.5 million Americans are infected with the same virus (The number is likely to be 15 million in maximum.) and more than 5 million Europeans are HCV patients.

HCV is a member of the Flaviviridae family. More specifically, HCV has about 9.5 kb sized (+)-RNA (single stranded positive-sense RNA) genome inside its envelope. RNA genome consists of an untranslational region at 5' and 3' ends (UTR) and a long open reading frame (ORF). This ORF is expressed as a polyprotein including 3,010 to 3,040 amino acids by host cell enzymes and divided into 3 structural proteins and 6 nonstructural proteins by host cell enzymes and its own protease. Also, there is a uniformly conserved region in the 5' end and the 3' end of the genome, respectively. This region is believed to play an important role for protein expression and RNA replication of the virus.

The long ORF is expressed as a polyprotein, and through co-translational or post-translational processing, it is processed into structural proteins, i.e. core antigen protein (core) and surface antigen protein (E1, E2), and nonstructural proteins, NS2 (protease), NS3 (serine protease, helicase), NS4A (serine protease cofactor), NS4B (protease cofactor, involved in resistance), NS5A, and NS5B (RNA dependent RNA polymerase, RdRp), each contributing to replication of virus. The structural proteins are divided into core, E1, and E2 by signal peptidase of the host cell. Meanwhile, the nonstructural proteins are processed by serine protease (NS3) and cofactor (NS2, NS4A, and NS4B) of the virus. The core antigen protein together with surface antigen protein of the structural protein compose a capsid of the virus, and the nonstructural proteins like NS3 and NS5B play an important role of the RNA replication of the virus (Reference: Bartenschager, R., 1997, Molecular targets in inhibition of hepatitis C virus replication, *Antivir. Chem. Chemother.* 8: 281-301).

Similar to other Flaviviruses, the 5' and 3' ends of the virus RNA has a uniformly conserved untranslational region (UTR). Generally, this region is known to play a very important role in replication of the virus. The 5' end has 5'-UTR composed of 341 nucleotides, and this part has the structure of 4 stem and loop (I, II, III, and IV). Actually, this functions as an internal ribosome entry site (IRES) necessary for translation processing to express protein. Particularly, the stem III, which has the biggest and the most stable structure with conserved sequence, has been reported to play the most essential part for ribosome binding. In addition, a recent study tells that the virus proteins are expressed by initiation of translational processing from AUG that exists in the single RNA of the stem IV (Reference: Stanley, M. Lemon and Masao Honda, 1997, Internal ribosome entry sites within the RNA genomes of hepatitis C virus and other Flaviviruses, seminars in Virology 8:274–288).

Moreover, the 3' end has 3'-UTR composed of 318 nucleotides. This part is known to play a very important role in the initiation step of binding of NS5B, an essential enzyme of RNA replication. The 3'-UTR, according to the sequence and tertiary structure, is composed of three different parts: -X-tail-5' starting from the 5'end to 98th nucleotide (98nt), -poly(U)- having UTP consecutively, and the rest of 3'-UTR-. More specifically, X-tail-5' part consists of 98 nucleotides having a very conserved sequence, and has three stem and loop structures, thereby forming a very stable tertiary structure. Probably, this is why X-tail-5' part is considered very essential of NS5B binding. Also, it is reported that -poly(U)- part induces a pyrimidine track, facilitating RNA polymerase effect. Lastly, the rest part of 3'-UTR part has the tertiary structure of loop and plays an important role in NS5B binding. However, its structure is known somewhat unstable. Overall, the 3'end region of HCV RNA is known to have an essential structure in NS5B binding when the RNA replication starts (Reference: Yamada et al., 1996, Genetic organization and diversity of the hepatitis C virus genome, *Virology* 223:255–281).

Among other enzymes of HCV, NS5B is the one that is directly involved in RNA replication and thus it is very important. NS5B is an enzyme consisting of 591 amino acids having the molecular weight of about 68 kDa. There are two RNA-binding domains (RBD), i.e. RBD1 and RBD2, in the NS5B enzyme. RBD1 exists between the amino acid numbers 83 and 194, and RBD2 exists between the amino acid numbers 196 and 298. Meanwhile, essential motif amino acids for RNA binding and activity are 'Asp' (amino acid number 220), 'Gly' (amino acid number 283), 'Gly' (amino acid number 317), 'Asp' (amino acid number 318), 'Asp' (amino acid number 319), and 'Lys' (amino acid number 346). Further, provided that there exists a RNA template of the virus itself, this enzyme can lead a polymerization reaction without another primer (Reference:

Lohmann, V. et al., 1997, Biochemical properties of hepatitis C virus NS5B RNA dependent RNA polymerase and identification of amino acid sequence motifs essential for enzymatic activity, *J. viral.* 71:8416–8428).

RNA genome of HCV was isolated in 1989 by molecular cloning (Reference: Choo, Q-L, et al., 1989, Isolation of a cDNA clone derived from a blood-borne non-A, non-B viral hepatitis genome. *Science* 244:359–362). Although there have been a number of molecular biological researches on HCV from that point, there were always limitations due to lack of more effective cell culture systems and animal models. Fortunately, the above problem has been somewhat resolved by the introduction of a hepatoma cell line which made it possible to replicate HCV more stably (Reference: Lohmann, V., F. Korner, J-O Koch, U. Herian, L. Theilmann, R. Bartenschlarger, 1999, Replication of subgenomic hepatitis c virus RNAs in a hepatoma cell line. *Science* 285: 110–113).

So far, no one has actually found vaccine or therapeutics that is very effective for HCV. Hence, many pharmaceutical companies and institutes around the world are now trying to develop therapeutics and prevention of hepatitis C. HCV patients are prevalent in the world, and its frequency to be progressed to hepatic cirrhosis and/or liver cancer is much higher than HBV. Also, despite its high frequency to be progressed to chronic hepatitis, the research on infection mechanism of the virus is still under progress. People are infected with HCV through blood transfusion or medication via phleboclysis or tattooing, but most of cases HCV infection takes place through a direct blood contact. However, 40–50% of the HCV patients still do not exactly know how they became infected. In view of this situation, it is a very urgent matter to develop a new vaccine and therapeutics to treat the diseases. In general, HCV exist as diverse genotypes between strains and mutation. Once a person is progressed to chronic hepatitis from HCV, it is not hard to see reinfection or coinfection owing to genetic variants. Because of this, few succeeded to develop an effective vaccine for HCV. Another example of HCV treatments is using alpha interferon (α-interferon). However, this approach proved to be not that good because the effects of alpha interferon on different HCV genotypes were very diverse and when its administration was discontinued, patients relapsed into hepatitis C in most of cases. Hence it will be important to develop an inhibitor that binds only to a particular HCV protein in order to control HCV replication. The best targets of such research are NS3 protease/helicase and NS5B RNA polymerase of HCV. These enzymes are very useful for developing anti-HCV agent since these types of enzyme is not necessary for the host cell but essential for its own replication. In other words, NS5B of HCV (RNA dependent RNA polymerase) is an essential enzyme for HCV, and this makes the enzyme a good target for suppressing the replication of HCV.

Now that HCV is not easily treated by vaccine, a new therapy using α-interferon and Ribavirin was introduced. But this, too, caused side effects and was not effective for treating hepatitis C. For example, about 25% of HCV patients showed no reaction to the interferon therapy, and about 25% reacted to it only for temporarily and relapsed into hepatitis C. The rest 50% of the patients maintained ALT at a normal level after the treatment was completed and their HCV RNA became negative. However, 50% of them relapsed into hepatitis C within 3–6 months. In short, only 25% of the HCV patients showed sustained response for more than 6 months. Meanwhile, the most HCV subtype found in patient world wide is 1 (1a, 1b) that is not easily treated by interferon, compared to 2 and 3 subtypes. In case of combination therapy with interferon and ribavirin, the treatment effect was doubled. What is known about ribavirin is that when it was used alone, it showed little effect on HCV and rather, caused side effects like erythroclastic anemia. Thus ribavirin was prescribed only when the interferon therapy was no good or relapsed into hepatitis C again. So far, no one actually developed an antiviral agent for treating hepatitis C by suppressing the replication of HCV.

The present invention, therefore, is directed to develop a non-nucleoside small molecule having low toxicity and side effect but manifesting excellent antiviral activity against HCV, by studying any possible compound that inhibits the activity of the recombinant HCV RNA polymerase (NS5B, RNA polymerase).

After making so much efforts for developing a compound with excellent anti-viral activity against HCV as an attempt to develop a new HCV therapeutics having low toxicity and side effect, the inventors finally succeeded to synthesize a new 6-methylpyridine derivative represented by the above chemical formula I and proved that this compound is indeed very effective for inhibiting the replication of HCV.

DISCLOSURE OF INVENTION

It is, therefore, an object of the present invention to provide 6-methylpyridine derivative, which is effective for inhibiting the replication of HCV, and pharmaceutically acceptable salts thereof and a method for preparing the compound.

Another object of the present invention is to provide a pharmaceutical composition comprising the above compound as an effective component, which has low side effect and is economical, for prevention and treatment of hepatitis C.

To achieve the above objects, the present invention provides novel 6-methylpyridine derivative, represented by the formula I shown below and its pharmaceutically acceptable salts.

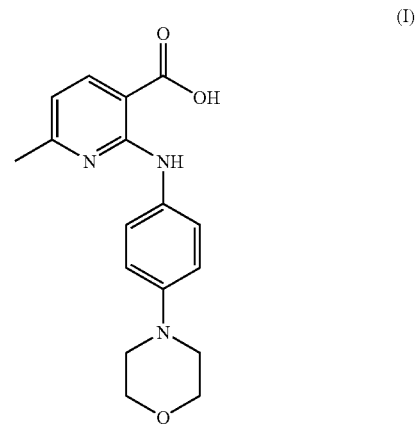

(I)

As aforementioned, the above compound can be used in form of pharmaceutically acceptable salts. As for that salts, an acid addition salts that are prepared by pharmaceutically acceptable free acids are available. The compound with the chemical formula I can make pharmaceutically acceptable acid addition salts following the conventional method in the related art. As for free acids, both organic acids and inorganic acids can be used. For instance, inorganic acids include hydrochloric acid, hydrobromic acid, sulfuric acid, and phosphoric acid. Organic acids include citric acid, acetic acid, lactic acid, tartaric acid, maleic acid, fumaric acid, formic acid, propionic acid, oxalic acid, trifluoroacetic acid, benzoic acid, gluconic acid, methanesulfonic acid, glycolic acid, succinic acid, 4-toluenesulfonic acid, glutamic acid or aspartic acid.

Another aspect of the present invention provides a method for preparing 6-methylpyridine derivative, represented by the following scheme:

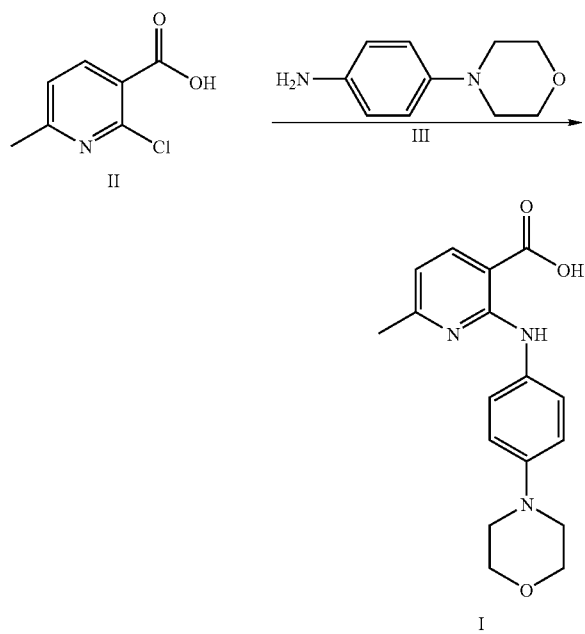

As shown in the above scheme, 6-Methylpyridine derivative of the present invention, represented by chemical formula I, are prepared by reacting 2-chloro-6-methylnicotinic acid of the chemical formula II with 4-(4-morpholino) aniline of the chemical formula III. The starting material, i.e. 2-chloro-6-methylnicotinic acid of the chemical formula II, and the reactant, i.e. 4-(4-morpholino)aniline of the chemical formula III are commercially available chemicals for anyone to get.

To give more details on the preparation method described above, the reactions are performed in organic solvents such as methanol, ethanol, isopropanol, dichloromethane, chloroform, acetonitrile, N,N-dimethylformamide, acetone and the like, and in the presence of the weak tertiary organic bases such as pyridine, 2,6-lutidine, 4-dimethylaminopyridine, N,N-dimethylaniline and the like, for a relatively long period of time, namely one day to 6 days at a temperature in the range of 40–80° C.

The present invention also provides the pharmaceutical compositions for treatment and prevention of hepatitis C, which contains the 6-methylpyridine derivative represented by the chemical formula I and/or its pharmaceutically acceptable salts as an active ingredient.

The compounds of the chemical formula I as the therapeutics for hepatitis C may be administered orally as well as through other routes in clinical uses, and can be used in form of general drugs. If it needs to be prepared, a generally used diluent including filler, builder, binder, humectant, dis-integration agent or surfactant or excipient can be employed. In the meantime, the solid preparation for oral administration includes tablets, pills, powder, granules or capsules. This solid preparation involves the compound of the chemical formula I and more than one excipient, for example, starch, calcium carbonate, sucrose or lactose, or gelatin. As for the liquid preparation for oral administration, suspension, solution, oily medicine or syrup can be used, but it can also employ a simple diluent, namely water, liquid paraffin, or other kinds of excipient, e.g. humectant, sweetening agent, odorant, or preservative. As for liquid preparation for non-oral administration, sterilized water solution, non-aqueous solvent, suspension or oily medicine. Preferably used non-aqueous solvent and suspension is propylene glycol, polyethylene glycol, vegetable oil like olive oil, and injectable esters like ethyl oleate.

The effective dose of the compound of the chemical formula I is controlled depending on the patient's sex, age and condition. In general, it can be dosed to adults 10–1000 mg/day, more preferably 20–500 mg/day, or one to three times dividedly per day.

DETAILED DESCRIPTION OF THE PREFERRED EMBODIMENT

Now, the present invention is explained in detail by the following examples. However, the examples are provided for illustration of the present invention not for limitation thereof.

EXAMPLE 1

Preparation of 6-methyl-2-[4-(4-morpholino)anilino] nicotinic acid 5 g of 2-chloro-6-methylnicotinic acid, 5.45 g of 4-(4-morpholino) aniline, and 7.2 ml of pyridine were added to 100 ml of chloroform. The mixture was heated to 60° C. and stirred for five days at 60° C. When the reaction was completed, the reaction mixture was cooled to room temperature and a little amount of precipitated solid was filtered and washed with 10 ml of chloroform to remove impurities. The solvent chloroform was concentrated under reduced pressure and the residue was crystallized with 60 ml of methanol, and stirred for 1 hour. The product was filtered, washed twice with 10 ml of methanol and dried in vacuo at 35–45° C. to give 7.31 g of the desired compound (80% yield).

m.p.: 220–221° C.

$^1$H-NMR (DMSO-$d_6$), ppm: δ 2.39 (s, 3H), 3.04 (t, 4H), 3.73 (t, 4H), 6.61 (dd, 1H), 6.89 (d, 2H), 7.57 (dd, 2H), 8.05 (dd, 1H), 10.21 (s, 1H)

EXPERIMENTAL EXAMPLE 1

Test of Inhibitory Effect on Activity of HCV RNA Polymerase (RNA Dependent RNA Polymerase, NS5B) In Vitro The following in vitro experiments were conducted to find out the effect of inhibition activity of compounds of the present invention against HCV RNA Polymerase (RNA dependent RNA polymerase, NS5B).

Construct of Recombinant HCV RNA Polymerase

HCV RNA polymerase was prepared as follows.

HCV cDNA was obtained from the blood of HCV-1b type HCV patient and NS5B region (1773 bps) was amplified by PCR and cloned into pVLHIS, a baculovirus transfer vector, to prepare recombinant transfer vector. The prepared transfer vector and the wild-type AcNPV vector were cotransfected into Sf 9 cell line to yield recombinant baculovirus with the histidine-tagged recombinant vector pVLHIS-NS5B. Sufficiently cultured insect cells were infected with the resulting recombinant baculovirus and cultured in Grace' medium containing 10% FBS for 3–4 days. The culture broth was centrifuged to obtain only the infected cells. The cells were washed three times with PBS and resuspended in binding buffer [50 mM Na-phosphate (pH 8.0), 30 mM NaCl, 10 mM imidazole, 1 mM DTT, 10% glycerol, 1% NP-40], sonicated and the clearized lysate was obtained. Recombinant NS5B was purified by affinity column chromatography using a Ni-NTA His bind resin (Novagen) to produce pure NS5B protein. The $(His)_6$-tagged NS5B was bound to Ni-NTA resin and washed with the binding buffer containing 50 mM imidazole. The bound NS5B was eluted with the binding buffer containing imidazole in a step-gradient manner (100–300 mM). The NS5B protein fractions were dialyzed against buffer [50 mM Tris-HCl, 50 mM NaCl, 1 mM DTT, 5 mg $MgCl_2$, 10% glycerol], followed by at −70° C. in a small aliquot.

Construct of RNA Template Containing HCV 3' end (3'-UTR)

The RNA Template containing HCV 3' end (3'-UTR) was prepared as follows.

The 3'UTR cDNA (220 bp) of HCV was obtained from 1b HCV RNA of the blood of a hepatitis C patient by PCR and cloned into pcDNA3 vector. Linearized DNA fragment containing 3'-UTR was prepared using the restriction enzyme, EcoRI and used as a temperate for in vitro transcription using T7 RNA ploymerase to prepare RNA fragment containing 3'-UTR.

Measurement of Inhibitory Activity of Compounds of the Present Invention

Measurement of Inhibitory Activity of Compounds of the Present Invention on Recombinant HCV RNA Polymerase In Vitro In Vitro inhibitory activity of the compounds of the present invention against recombinant HCV RNA polymerase was measured as follows.

A streptavidin-coated well plate was prepared suitable for the sample to be examined. 25 µl of 2× assay buffer [50 mM Tris-Cl (pH 7.5), 100 mM NaCl, 10 mM $MgCl_2$, 20 mM KCl, 1 mM EDTA, 1 mM DTT] and 10 µl of purified HCV RNA polymerase 200 ng and 3'-UTR template RNA were added to each well. Then, 5 µl of the sample to be examined was added to have final concentrations of 10, 1, 0.1 and 0.01 µg/mL. Finally, 10 µl of a reactant solution containing DIG-(digoxigenin)-UTP, biotin-UTP, ATP, CTP, GTP, and UTP as a nucleotide for the ploymerase reaction with the RNA template of HCV 3'-UTR RNA was added to each well. The reaction mixture was incubated at 22° C. for 60 minutes. By the action of HCV polymerase, newly generated RNAs including UTP conjugated with biotin and DIG were copied and these new RNAs could bind to streptavidin coated on the well by biotin-conjugated UTP. After completion of the reaction, the plate was washed three times with 200 µl of a washing buffer (pH 7.0, Roche Co.) to remove unreacted substances and impurities. Then, 100 µl of the secondary antibody anti-DIG-POD (peroxidase, Roche Co.) was added to each well and incubated at 37° C. for 1 hour. Again, the well plate was washed with the washing buffer. Finally, 100 µl of $ABTS^R$ (Roche Co.) as a POD substrate was added to each well and reacted for 15 to 30 minutes. The optical density (OD) was measured using an ELISA reader (Bio-Tek instrument Co.) at 405 nm. The inhibitory effect on the activity of HCV polymerase was calculated by subtracting the OD of the positive control without the sample. The results are shown in Table 1 below.

TABLE 1

| Test compound | Inhibition of activity of HCV RNA polymerase (%) | | | |
|---|---|---|---|---|
| | 10 µg/ml | 1 µg/ml | 0.1 µg/ml | 0.01 µg/ml |
| Example 1 | 99 | 82 | 65 | 46 |

As can be seen from the above table, it is proved that the compound according to the present invention show excellent inhibitory effects on activity of HCV RNA polymerase which plays an important role in reproduction of HCV, thereby inhibiting replication of HCV by this property. Also, the compounds according to the present invention can be advantageously used as a therapeutic or prophylactic agent of hepatitis C.

EXPERIMENTAL EXAMPLE 2

Cytotoxicity Assay

To find out cytotoxicity of 6-methylpyridine derivative of the chemical formula 1, an in vitro experiment was conducted on the basis of the generally known MTT assay using HepG 2 cell line. In result, it was proved that $CC_{50}$ value of the compound employed for the experiment was greater than 100 µg/ml, indicating that it is safe compound with extremely low cytotoxicity.

INDUSTRIAL APPLICABILITY

As described above, the novel 6-methylpyridine derivative according to the present invention represented by the chemical formula I have excellent inhibitory effect on replication of hepatitis C virus and low cytotoxicity. Therefore, they can be advantageously used as a therapeutic or prophylactic agent of hepatitis C.

What is claimed is:

1. A 6-methyl-2-[4-(4-morpholino)anilino]nicotinic acid represented by the following formula 1:

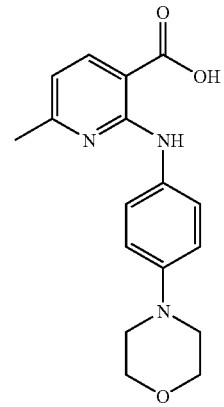

or pharmaceutically acceptable salts thereof.

2. A method for preparing 6-methyl-2-[4-(4-morpholino) anilino]nicotinic acid by reacting 2-chloro-6-methylnicotinic acid of chemical formula II with 4-(4-morforino)aniline of chemical formula III as shown in the following scheme:

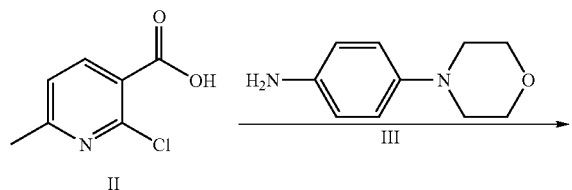
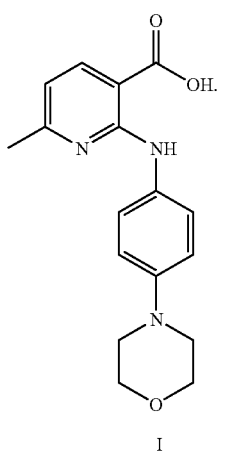
3. A pharmaceutical composition for the treatment of hepatitis C comprising 6-methyl-2-[4-(4-morpholino)anilino]nicotinic acid represented by the following formula 1:
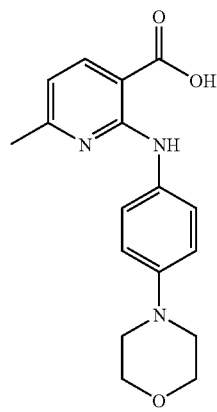
or pharmaceutically acceptable salts thereof as an active ingredient.
* * * * *

UNITED STATES PATENT AND TRADEMARK OFFICE
CERTIFICATE OF CORRECTION

PATENT NO. : 7,244,731 B2 Page 1 of 1
APPLICATION NO. : 10/528461
DATED : July 17, 2007
INVENTOR(S) : Kim et al.

It is certified that error appears in the above-identified patent and that said Letters Patent is hereby corrected as shown below:

Column 8, Line 66,
Please delete "with 4-(4-morforino)aniline of"
and
replace with
-- with 4-(4-morpholino)aniline of --

Signed and Sealed this

Eighteenth Day of September, 2007

JON W. DUDAS
*Director of the United States Patent and Trademark Office*